(12) United States Patent
Sierro et al.

(10) Patent No.: US 7,011,521 B2
(45) Date of Patent: Mar. 14, 2006

(54) DENTAL HANDPIECE

(75) Inventors: Alexandre Sierro, Celigny (CH); Lutz Beerstecher, Borex (CH)

(73) Assignee: Ferton Holding S.A., (CH)

( * ) Notice: Subject to any disclaimer, the term of this patent is extended or adjusted under 35 U.S.C. 154(b) by 72 days.

(21) Appl. No.: 10/388,030

(22) Filed: Mar. 12, 2003

(65) Prior Publication Data
US 2003/0180684 A1 Sep. 25, 2003

(30) Foreign Application Priority Data
Mar. 22, 2002 (DE) .............................. 102 12 925

(51) Int. Cl.
*A61C 3/02* (2006.01)
(52) U.S. Cl. ...................................... 433/88
(58) Field of Classification Search ............... 433/88, 433/80, 82; 451/75, 76, 101, 102
See application file for complete search history.

(56) References Cited

U.S. PATENT DOCUMENTS

| | | | |
|---|---|---|---|
| 4,413,758 A * | 11/1983 | Walters | 222/195 |
| 4,494,932 A * | 1/1985 | Rzewinski | 433/88 |
| 5,857,851 A * | 1/1999 | Chavanne | 433/88 |
| 5,961,326 A * | 10/1999 | Johnston et al. | 433/80 |
| 6,220,772 B1 * | 4/2001 | Taylor | 401/176 |
| 6,390,816 B1 * | 5/2002 | Ito et al. | 433/88 |
| 2001/0031441 A1 | 10/2001 | Ito et al. | 433/88 |
| 2002/0137005 A1 | 9/2002 | Cevey et al. | 433/88 |

FOREIGN PATENT DOCUMENTS

| | | |
|---|---|---|
| DE | 10113289 | 10/2002 |
| EP | 0 097 288 B1 | 1/1984 |
| EP | 0834291 | 4/1998 |
| EP | 0870477 | 10/1998 |

OTHER PUBLICATIONS

European Search Report dated May 15, 2003.

* cited by examiner

*Primary Examiner*—Melba N. Bumgarner
(74) *Attorney, Agent, or Firm*—Ostrolenk, Faber, Gerb & Soffen, LLP

(57) ABSTRACT

A dental handpiece for use with a device for treatment of teeth by a jet of an abrasive powder mixed with air and water has a first one-way valve in a first supply line for pressurised air connected to an integrated powder container of a gripping sleeve and at least a first filter is further provided in this first supply line at a position upstream of the first one-way valve and downstream of a connecting end where the supply line connects with a common supply for air and water which is provided at the rearward end of the gripping sleeve. A second filter is provided at a position downstream of the first one-way valve in the first supply line and a second one-way valve is provided in a second supply line for water together with a third filter. The first and third filters each have a fine-meshed screen body. The second filter has a microporous sintered metallic body or a microporous plastic body.

28 Claims, 2 Drawing Sheets

DENTAL HANDPIECE

FIELD OF THE INVENTION

The present invention relates to a dental handpiece for use with a device for treatment of teeth by means of a jet of an abrasive powder mixed with air and water.

BACKGROUND OF THE INVENTION

U.S. Pat. No. 6,416,321 and the corresponding European Patent EP 0 834 291 B1 disclose a dental handpiece of the before mentioned kind which comprises a gripping sleeve that is provided with an integrated powder container for storing a predetermined amount of powder as an abrasive material for the polishing or cleaning of teeth in the course of a singular treatment of teeth. The powder container is substantially cup-shaped and forms the rearward end of the gripping sleeve with which it is coaxially screw-connected at an enlarged portion of the gripping sleeve. The gripping sleeve is branched at its enlarged portion under an acute angle with respect to its longitudinal axis for providing a coupling connection for a common supply means for air and water at a rearward end of the gripping sleeve. Pressurised air is supplied to the powder container via a first supply line while water is supplied via a second supply line to a multiple nozzle arrangement which is provided at a forward spray head of the gripping sleeve. A transfer line for powder mixed with air connects the powder container with this multiple nozzle arrangement. For avoiding a backflow of the powder particles that are taken up within the powder container by the pressurised air which is supplied by the common supply means for air and water via the first supply line there is also provided a one-way valve means which with the design of a ball valve forms a functional part of the coupling connection. The ball valve is arranged in an insert member forming the connecting end of the first supply line for pressurised air in such manner that it will prevent any backflow of the pressurised air from the powder container back to the coupling connection for avoiding any contamination of its different coupling parts by the abrasive powder particles that will accompany such backflow.

U.S. Pat. No. 5,857,851 and its corresponding European Patent EP 0 870 477 B1 disclose a dental handpiece of a similar design and provided with an integrated powder container that is formed as a closed hollow body of rotation acting as a whirl chamber spatially in all directions. The powder container is arranged substantially at half length of a gripping sleeve which at its axial rearward end is provided with a coupling means of a turbine in-line quick coupling of a common supply means for air and water. A first supply line for pressurised air comprises a tubular piece which is connected to the powder container. A second tubular piece serving as a transfer line for powder mixed with air connects the powder container with a multiple nozzle arrangement at a forward spay head of the gripping sleeve. A second supply line for water is further connected to the same multiple nozzle arrangement.

German Patent Publication DE 101 13 289 A1 discloses a dental spray device. A separate powder reservoir is interconnected with a supply line for pressurised air and connects via a transfer line for powder mixed with air to a dental handpiece having a multiple nozzle arrangement at a forward spray head of a handle. A supply line for water is further connected to the same multiple nozzle arrangement. The supply line for pressurised air is provided at a position upstream of the powder reservoir with a condensate separator and a one-way valve that are arranged in series and serving the purpose of supplying only dry air to the powder reservoir.

STATEMENT OF THE INVENTION & ADVANTAGES

An object of the present invention is to provide a dental handpiece for use with a device for treatment of teeth by means of a jet of an abrasive powder mixed with air and water which provides an improved protection for its common supply means for air and water which is connected to the rearward end of the gripping sleeve.

It is a further object of the present invention to provide a dental handpiece of the kind as above referred which when having one-way valve means in a supply line for pressurised air will prevent any contamination of the one-way valve means by powder particles with which any backflow of the pressurised air from the powder container would be laden.

In accordance with the present invention a dental handpiece of the general kind as above described has a least a first filter means which is provided in the supply line for pressurised air at a position upstream of the one-way valve means and downstream of its connecting end to the common supply means for air and water. Preferably a second filter means is further provided in the same supply line for pressurised air at a position downstream of the one-way valve means and upstream of its delivery end which is connected to the powder container, whereby the first filter means should comprise of a fine-meshed screen body while the second filter means should comprise a microporous sintered metallic body or a microporous plastic body.

With a dental handpiece according to the present invention the first filter means which is provided at a position upstream of the one-way valve means in the supply line for pressurised air serves the primary purpose of preventing any contamination with which the in-flowing air could be laden to reach the one-way valve. This first filter means will also prevent water which could be present at the connecting end of the supply line for pressurised air to reach the powder container. The larger water droplets upstream of the first filter means will be disintegrated by the same and a gaseous condition of the water will be obtained which will be harmless to the powder in the powder container. This action of the first filter means will be further assisted by the second filter means at the position downstream of the one-way valve whereby the second filter means also prevents any backflow of powder. An optimum protection of the one-way valve means will therefore be obtained which will allow to use a simple and inexpensive "duck-bill" one-way valve means for use with the dental handpiece according to the present invention as a replacement for other more expensive and trouble causing types of such valves.

Further features and advantages of the inventive dental handpiece will become apparent from the following detailed description of a preferred embodiment as schematically illustrated in the drawing.

BRIEF DESCRIPTION OF THE DRAWINGS

The invention will now be described by way of example with reference to the accompanying drawings, in which.

DETAILED DESCRIPTION OF THE PREFERRED EMBODIMENT

Figure 1:
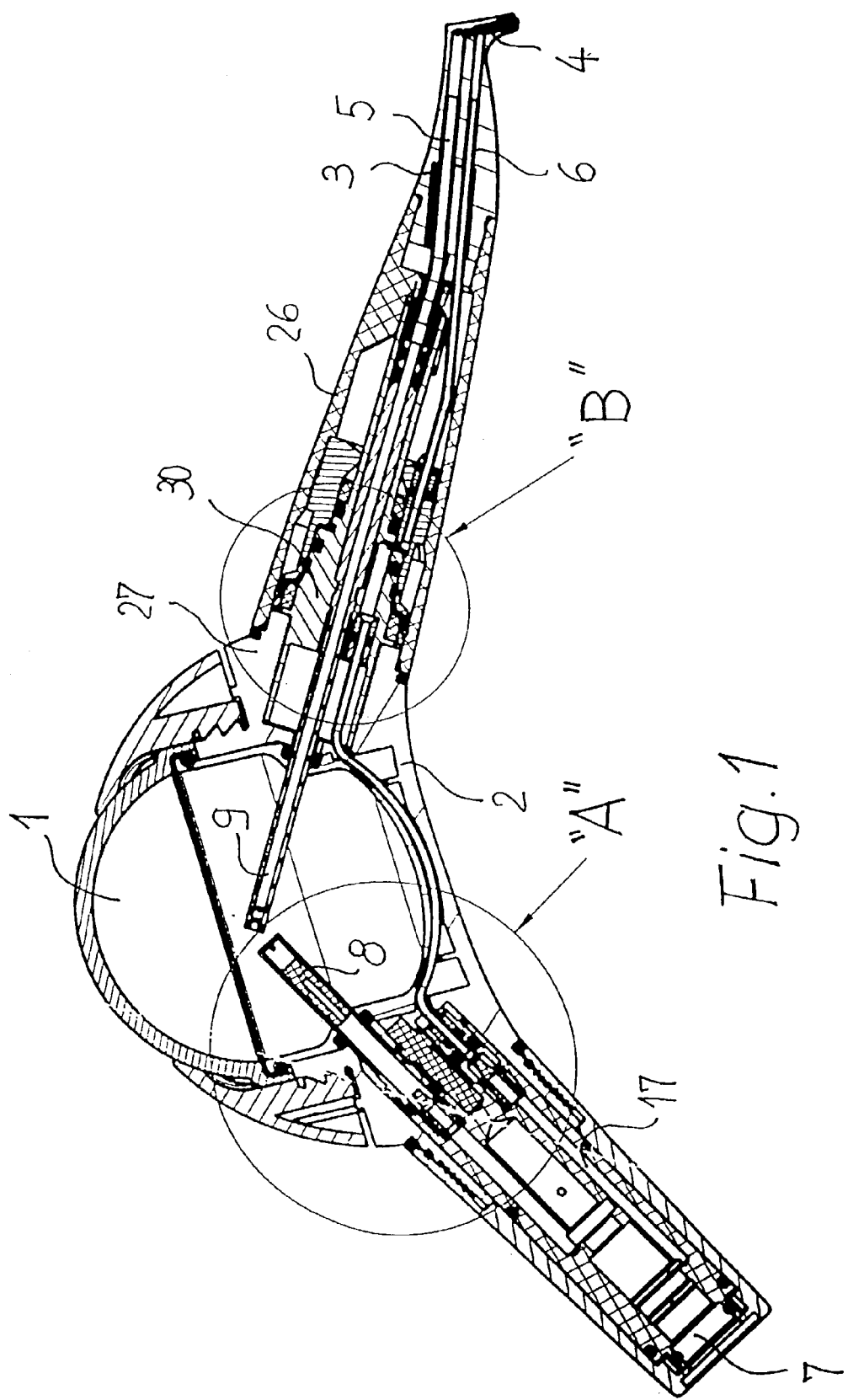
FIG. 1 is a sectional illustration of the handpiece.

The dental handpiece as shown in FIG. 1 with an overall sectional view is substantially identical with the dental handpiece as shown and described in more detail in U.S. Pat. No. 5,857,851 so that for further details reference should be made to this document.

The dental handpiece according to the present invention therefore comprises as well an integrated powder container 1 which is formed as a closed hollow body of rotation acting as a whirl chamber spatially in all directions. The powder container is arranged substantially at half length of a gripping sleeve 2 which at its forward end is provided with a nozzle piece 3 that incorporates a multiple nozzle arrangement 4. The multiple nozzle arrangement 4 is interconnected with two separate 1o supply lines 5 and 6 for being supplied with powder mixed with air and with water respectively. The powder is stored in the integrated powder container 1 while pressurised air and water are supplied via a sealed common supply connection 7 at the rearward end of the gripping sleeve. The pressurised air is supplied to the powder container 1 via the delivery end of a tubular piece 8 for being mixed with the powder. A mixture of air and powder is discharged from the powder container 1 via a discharge end of a further tubular piece 9 which is connected to the transfer line 5 leading to the multiple nozzle arrangement 4 of the nozzle piece 3 forming a forward spray head of the gripping sleeve.

Figure 2:
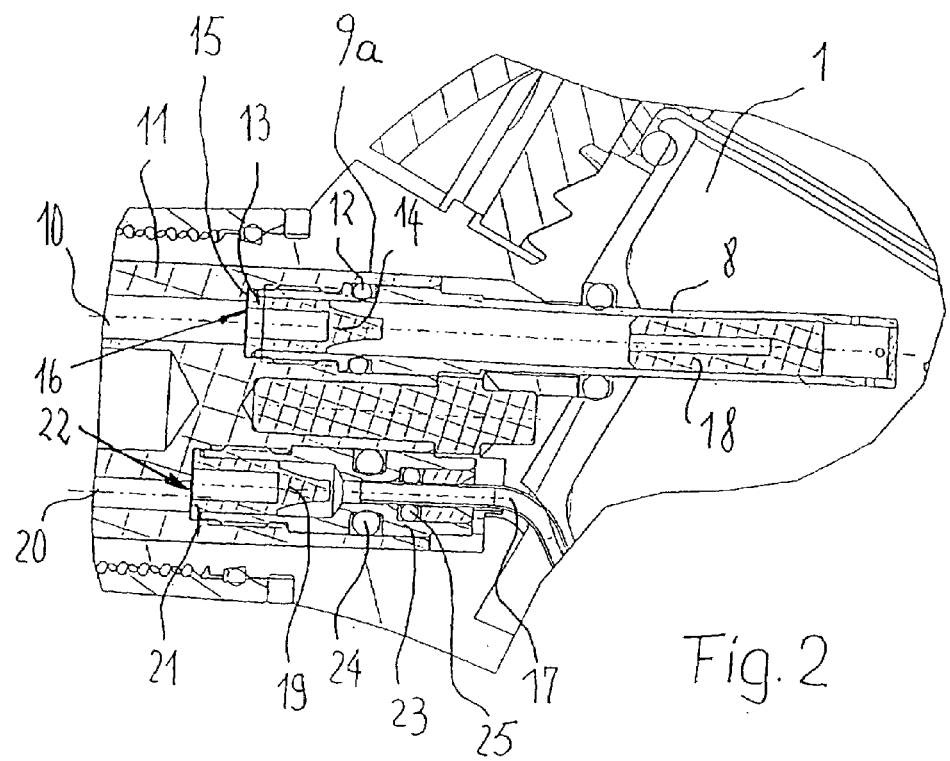
FIG. 2 is an enlarged illustration of the encircled detail A in FIG. 1.

As illustrated in more detail in FIG. 2 tubular piece 8 is inserted into the larger diameter 9a of a stepped bore 10 which is formed in an insert member 11 of the rearward end of the gripping sleeve 2. The tubular piece 8 is sealed against the larger diameter 9a of the stepped bore by means of an annular seal 12 and presses an annular flange 13 of an elastic "duck-bill" one-way valve body 14 against a stop shoulder 15 which is formed at the transition of the smaller diameter to the larger diameter of the stepped bore 10. The "duck-bill" one-way valve body 14 forms a one-way valve means which admits in-flow of pressurised air via the smaller diameter of the stepped bore 10 in the direction of the powder container 1 and prevents at the same time a backflow of the air. There is further provided a filter means 16 immediately upstream of the one-way valve means 14. The filter means 16 comprises a fine-meshed screen body which by means of the annular flange 13 is pressed against the stop shoulder 15. The filter means 16 serves the primary purpose of preventing an admission of contaminations towards the one-way valve means 14 whereby such contaminations could be present in the airflow of the interconnected common supply means for air and water. The filter means 16 further prevents an admission of water via the tubular piece 8 into the powder container 1 in case of a faulty transit of water at the upstream connecting end of the supply line 17 which downstream is further connected to the connecting supply line 6 of the multiple nozzle arrangement 4.

The double function of the filter means 16 is added by a further filter means 18 which is inserted into the delivery end of the tubular piece 8. The filter means 18 preferably comprises a microporous sintered metallic body or a same microporous plastic body which primarily provides a protection for the elastic material of the "duck-bill" one-way valve body 14. This further filter means 18 mainly serves the purpose of preventing a backflow of air from the powder container 1 towards the one-way valve means 14 for protecting the same in respect to the powder particles with which the pressurised air will be laden within the powder container 1. This further filter means 18 also prevents an admission of water which still should have passed the first filter means 16 and the "duck-bill" one-way valve body 14. The microporous structure of the filter means 18 will assist a final vaporation of the water into a gaseous condition so that the air supplied to the powder container 1 will be admitted in a fully dry condition.

FIG. 2 also illustrates the provision of a second one-way valve means in the supply line 17 for water which also comprises a "duck-bill" one way valve body 19. This second one-way valve means is also inserted into the larger diameter of a stepped bore 20 and comprises an annular flange 21 at which the valve body is pressed against a stop shoulder provided at the transition of the smaller diameter to the larger diameter of the stepped bore 20 by means of a sealed bushing 23 together with a filter means 22 which is arranged at an adjacent upstream position. The filter means 22 comprises a fine-meshed screen body of the same or a different kind as the filter means 16 and serves the purpose of preventing an admission of contaminations to the supply line 17. Supply line 17 is taken up by the bushing 23 which is inserted into the larger diameter of the stepped bore 20 together with an annular seal 24 for sealing the bushing against the larger diameter of the stepped bore. A further annular seal 25 seals the supply line 17 against the bushing 23.

Figure 3:
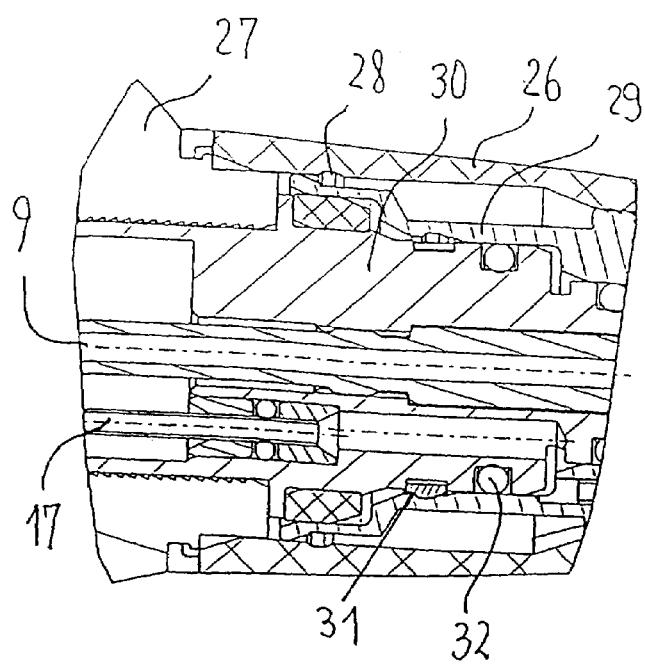
FIG. 3 is an enlarged illustration of the encircled detail B in FIG. 1.

As may be derived from the illustration in FIG. 3 it is shown that the nozzle member 3 which comprises the multiple nozzle arrangement 4 is mounted on a gripping member 26 which is rotatably centered on the exterior of the powder container 1 by means of a coaxial projection 27. The gripping member 26 is mounted on this projection 27 via a bearing 28 which is supported by a support body 29 which in turn is arranged on a coaxial projection 30 of the powder container 1. The projection 30 further centers the tubular piece 9 by which the powder mixed with air and discharged from the powder container 1 is further supplied via the connecting supply line 5 to the multiple nozzle arrangement 4 of the nozzle piece 3. The supply line 17 for water is as well passed through this projection 30 for its connection with its corresponding connecting supply line 6 of the multiple nozzle arrangement 4. The support member 29 is connected with the projection 30 via a snap-in locking means 31 and is mutually sealed by an annular seal 32.

We claim:

1. A dental handpiece for use with a device for treatment of teeth by means of a jet of an abrasive powder mixed with air and water, comprising:

a gripping sleeve having an integrated powder container for storing a predetermined amount of powder;

a first supply line for pressurised air connected to the powder container;

a transfer line for powder mixed with air connecting the powder container with a multiple nozzle arrangement at a forward spray head of the gripping sleeve;

a second supply line for water connected to the multiple nozzle arrangement; and a first one-way valve means in the first supply line at a position upstream of its delivery end which is connected to the powder container and downstream of its connecting end to a common supply means for air and water which is provided at the rearward end of the gripping sleeve;

at least a first filter means provided in the handpiece in the first supply line for pressurised air, at a position upstream of the first one-way valve means and downstream of its connecting end to the common supply means for air and water.

2. The dental handpiece according to claim 1, wherein a second filter means is provided in the first supply line at a position downstream of the first one-way valve means and upstream of its delivery end which is connected to the powder container.

3. The dental handpiece according to claim 2, wherein the second filter means comprises a microporous sintered metallic body or a microporous plastic body.

4. The dental handpiece according to claim 1, wherein a second one-way valve means is provided in the second supply line for water together with an additional filter means which is arranged at an upstream position thereof.

5. The dental handpiece according to claim 4, wherein the first filter means and the additional filter means each comprise a fine-meshed screen body.

6. The dental handpiece according to claim 4, wherein the first and the second one-way valve means are each inserted into a stepped bore of the adjacent first and second supply lines whereby a step formed at a transition between a larger diameter portion and a smaller diameter portion of the stepped bore provides a stop shoulder for the respective one-way valve means.

7. The dental handpiece according to claim 6, wherein an insert member which is inserted into the rearward end of the gripping sleeve is arranged for housing the first and second one-way valve means and the first filter means and additional filter means in two stepped bores which are arranged in parallel with each other.

8. The dental handpiece according to claim 6, wherein the first and second one-way valve means are each inserted into the larger diameter portion of the adjacent stepped bore and fixed therein by means of a sealed bushing.

9. The dental handpiece according to claim 8, wherein the first and second one-way valve means each comprise a "duck-bill" one-way valve body means.

10. The dental handpiece according to claim 6, wherein a second filter means is provided in the first supply line at a position downstream of the first one-way valve means and upstream of its delivery end which is connected to the powder container; and
wherein the first one-way valve means is fixed by a tubular piece which is inserted in a sealed manner into the larger diameter portion of the adjacent stepped bore of the first supply line, the tubular piece having a free end portion projecting into the powder container and comprising a delivery end in which the second filter means is arranged.

11. The dental handpiece according to claim 1, wherein the multiple nozzle arrangement comprises a nozzle member which by means of a gripping member is rotatably centered on the exterior of the powder container.

12. The dental handpiece according to claim 11, wherein the gripping member is mounted on a coaxial projection of the powder container, the coaxial projection comprising connecting supply lines for supplying the multiple nozzle arrangement of the nozzle member with the powder mixed with air and with water respectively, and further comprising a support member supporting a bearing means for the gripping member and being connected with the projection via a snap-in locking means.

13. The dental handpiece according to claim 1, wherein the first one-way valve means is inserted into a stepped bore of the first supply line whereby a step formed at a transition between a larger diameter portion and a smaller diameter portion of the stepped bore provides a stop shoulder for the first one-way valve means.

14. The dental handpiece according to claim 1, wherein the first filter means comprises a fine-meshed screen body.

15. A dental handpiece for use with a device for treatment of teeth by means of a jet of an abrasive powder mixed with air and water, comprising:
a gripping sleeve having an integrated powder container for storing a predetermined amount of powder;
a first supply line for pressurised air connected to the powder container;
a transfer line for powder mixed with air connecting the powder container with a multiple nozzle arrangement at a forward spray head of the gripping sleeve;
a second supply line for water connected to the multiple nozzle arrangement; and
a first one-way valve in the first supply line at a position upstream of its delivery end which is connected to the powder container and downstream of its connecting end to a common supply for air and water which is provided at the rearward end of the gripping sleeve;
at least a first filter provided in the handpiece in the first supply line for pressurised air, at a position upstream of the first one-way valve and downstream of its connecting end to the common supply for air and water.

16. The dental handpiece according to claim 15, wherein a second filter is provided in the first supply line at a position downstream of the first one-way valve and upstream of its delivery end which is connected to the powder container.

17. The dental handpiece according to claim 16, wherein the second filter comprises a microporous sintered metallic body or a microporous plastic body.

18. The dental handpiece according to claim 15, wherein a second one-way valve is provided in the second supply line for water together wit an additional filter which is arranged at an upstream position thereof.

19. The dental handpiece according to claim 18, wherein the first filter and the additional filter each comprise a fine-meshed screen body.

20. The dental handpiece according to claim 18, wherein the first and the second one-way valves are each inserted into a stepped bore of the adjacent first and second supply lines whereby a step formed at a transition between a larger diameter portion and a smaller diameter portion of the stepped bore provides a stop shoulder for the respective one-way valve.

21. The dental handpiece according to claim 20, wherein an insert member which is inserted into the rearward end of the gripping sleeve is arranged for housing the first and second one-way valves and the first filter and additional filter in two stepped bores which are arranged in parallel with each other.

22. The dental handpiece according to claim 20, wherein the first and second one-way valves are each inserted into the larger diameter portion of the adjacent stepped bore and fixed therein by a sealed bushing.

23. The dental handpiece according to claim 22, wherein the first and second one-way valves each comprise a "duck-bill" one-way valve body.

24. The dental handpiece according to claim 20, wherein a second filter is provided in the first supply line at a position downstream of the first one-way valve and upstream of its delivery end which is connected to the powder container; and
wherein the first one-way valve is fixed by a tubular piece which is inserted in a sealed manner into the larger diameter portion of the adjacent stepped bore of the first supply line, the tubular piece having a free end portion projecting into the powder container and comprising a delivery end in which the second filter means is arranged.

25. The dental handpiece according to claim 15, wherein the multiple nozzle arrangement comprises a nozzle member which is rotatably centered by a gripping member on the exterior of the powder container.

26. The dental handpiece according to claim 25, wherein the gripping member is mounted on a coaxial projection of the powder container, the coaxial projection comprising connecting supply lines for supplying the multiple nozzle arrangement of the nozzle member with the powder mixed with air and with water respectively, and further comprising a support member supporting a bearing for the gripping member and being connected with the projection via a snap-in lock.

27. The dental handpiece according to claim 15, wherein the first one-way valve is inserted into a stepped bore of the first supply line whereby a step formed at a transition between a larger diameter portion and a smaller diameter portion of the stepped bore provides a stop shoulder for the first one-way valve.

28. The dental handpiece according to claim 15, wherein the first filter comprises a fine-meshed screen body.

* * * * *